(12) United States Patent
Phukan et al.

(10) Patent No.: US 9,987,365 B2
(45) Date of Patent: Jun. 5, 2018

(54) PERSONAL CARE COMPOSITIONS WITH ACID FUNCTIONAL SILICONE BASED STRUCTURING AGENTS

(71) Applicant: Momentive Performance Materials Inc., Waterford, NY (US)

(72) Inventors: Monjit Phukan, Bangalore (IN); Anubhav Saxena, Bangalore (IN); Vasuki Kaushik, Bangalore (IN); Richard Anthony Presti, Airmont, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 165 days.

(21) Appl. No.: 15/017,767

(22) Filed: Feb. 8, 2016

(65) Prior Publication Data

US 2016/0228557 A1 Aug. 11, 2016

Related U.S. Application Data

(60) Provisional application No. 61/114,673, filed on Feb. 11, 2015.

(51) Int. Cl.
| | |
|---|---|
| *A61K 31/60* | (2006.01) |
| *A61K 47/24* | (2006.01) |
| *A61K 47/34* | (2017.01) |
| *A61K 9/00* | (2006.01) |
| *A61K 9/06* | (2006.01) |
| *A61K 8/58* | (2006.01) |
| *A61Q 19/00* | (2006.01) |
| *A61K 8/89* | (2006.01) |

(52) U.S. Cl.
CPC .............. *A61K 47/34* (2013.01); *A61K 8/585* (2013.01); *A61K 8/89* (2013.01); *A61K 31/60* (2013.01); *A61Q 19/00* (2013.01); *A61K 9/0014* (2013.01); *A61K 47/24* (2013.01)

(58) Field of Classification Search
CPC ........ A61K 31/60; A61K 47/24; A61K 47/34; A61K 8/585; A61K 8/89
See application file for complete search history.

(56) References Cited

U.S. PATENT DOCUMENTS

| | | |
|---|---|---|
| 5,232,689 A | 8/1993 | Katsoulis |
| 5,447,997 A | 9/1995 | Raleigh et al. |
| 5,993,832 A | 11/1999 | Lorant et al. |
| 6,867,317 B1 | 3/2005 | Buffa et al. |

FOREIGN PATENT DOCUMENTS

WO 2008046762 4/2008

OTHER PUBLICATIONS

Mintel, "Renovatingg double serum", (Aug. 2012), Database accession No. 1857550, XP00275632.
International Search Report and Written Opinion from PCT/US2016/016950 dated Oct. 21, 2016.

*Primary Examiner* — Alma Pipic
(74) *Attorney, Agent, or Firm* — Joseph S. Ostroff

(57) ABSTRACT

The invention is directed to personal care compositions comprising an acid functionality bearing silicone neutralized in situ with at least one aminosilane or a partially hydrolyzed aminosilane. The invention provides better stability to formulation in addition to improved delivery of hydrophilic actives from the formulation.

19 Claims, 4 Drawing Sheets

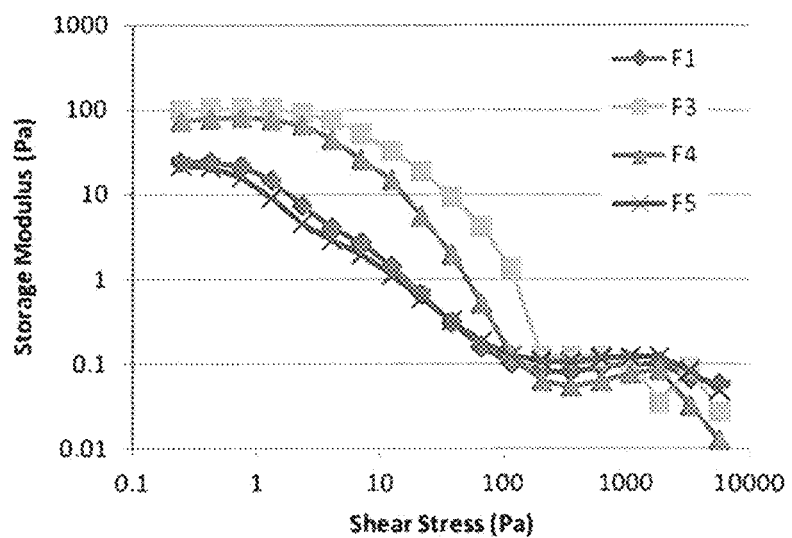
Fig1: Storage Modulus vs. shear stress for model HIP emulsions

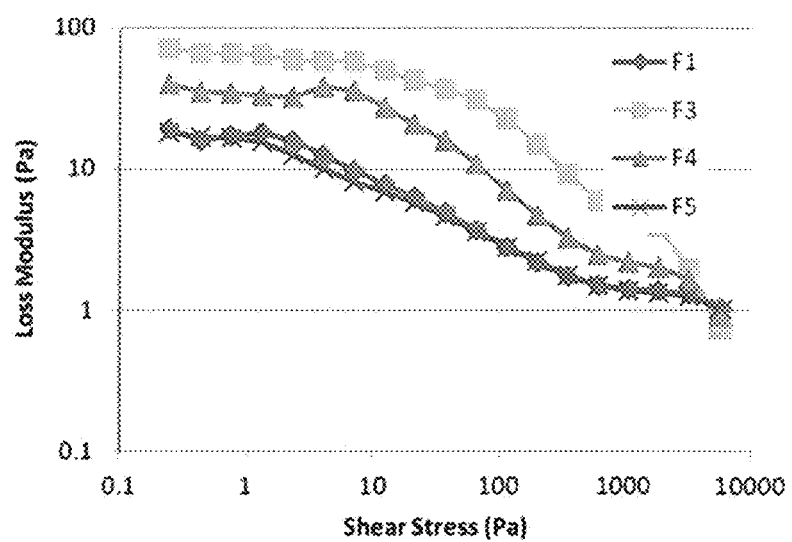
Fig2: Loss Modulus vs. shear stress for model HIP emulsions

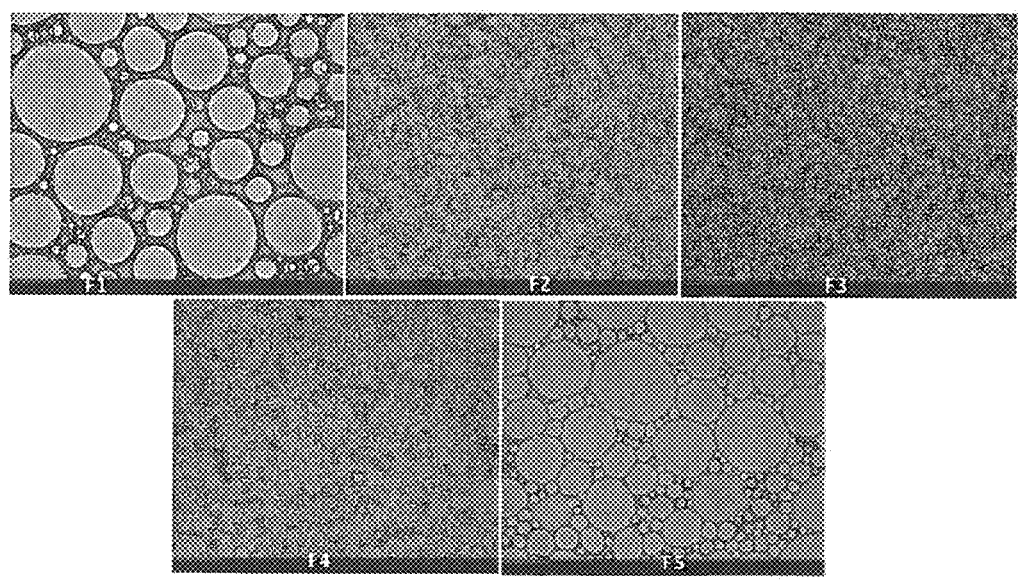
Fig3: Microscope images for model HIP emulsions

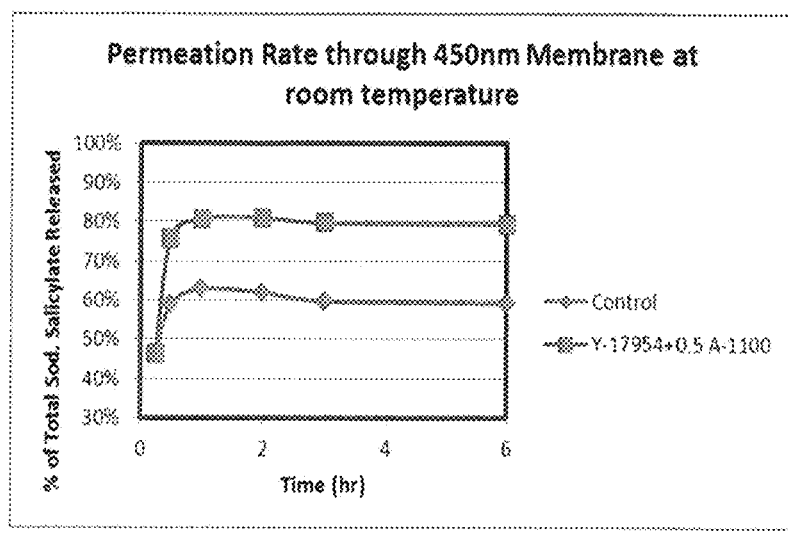
Fig4: Release of Sodium Salicylate from the skin cream formulations

PERSONAL CARE COMPOSITIONS WITH ACID FUNCTIONAL SILICONE BASED STRUCTURING AGENTS

FIELD OF THE INVENTION

The present invention relates to personal care compositions comprising an acid functionality bearing silicone neutralized in situ with at least one aminosilane or a partially hydrolyzed aminosilane. The invention provides better stability to formulation in addition to improved delivery of hydrophilic actives from the formulation.

BACKGROUND OF THE INVENTION

Anionically modified silicones are commonly used in personal care compositions to provide smoothness and feelings of softness. For example, carboxylated silicones have been reported to exhibit humectant-like characteristics to reduce the transepidermal water loss of skin. Furthermore, U.S. Pat. No. 5,993,832 discloses a cosmetic emulsions comprising of anionically modified silicone and acidic cosmeceutical actives to have better stability, sensorial and controlled release characteristics over traditional silicone surfactants.

However, these carboxylated silicones cannot provide high level of matrix building and therefore require other additives that may result into slower active compound diffusion from a high consistency formula.

SUMMARY OF THE INVENTION

In the present invention, there is provided a personal care composition comprising:

(a) at least one condensation effective aminosilane or hydrolysate thereof;

(b) at least one polyorganosiloxane represented by the formula (I):

  (I)

wherein:
$M^1 = R^1R^2R^3SiO_{1/2}$
$M^2 = R^4R^5R^6SiO_{1/2}$
$D^1 = R^7R^8SiO_{2/2}$
$D^2 = R^9R^{10}SiO_{2/2}$
$T^1 = R^{11}SiO_{3/2}$
$T^2 = R^{12}SiO_{3/2}$
$Q = SiO_{4/2}$ wherein
$R^1$, $R^2$, $R^3$, $R^5$, $R^6$, $R^7$, $R^8$, $R^{10}$ and $R^{11}$ are aliphatic, aromatic or fluoro containing monovalent hydrocarbon groups containing from 1 to about 60 carbon atoms;

$R^4$, $R^9$ and $R^{12}$ are independently a monovalent group bearing an acid functional group selected from the group consisting of -A-COOH, -A-PO$_3$H, -A-OPO$_3$H, or -A-SO$_3$H, wherein A is selected from the group consisting of a divalent hydrocarbon group having from about 1 to about 60 carbon atoms, optionally substituted with heteroatoms, and a divalent arylalkylene group having the general formula —(CHR')$_k$C$_6$H$_4$(CH$_2$)$_h$—, —CH$_2$CH(R')(CH$_2$)$_k$C$_6$H$_4$—, and —CH$_2$CH(R')(CH$_2$)$_h$C$_6$H$_3$R"—;

wherein R' is hydrogen or an aliphatic, aromatic or fluoro containing monovalent hydrocarbon group having from 1 to about 60 carbon atoms, h has a value of 0 to 20, k has a value of 0 to 10, specifically from about 0 to about 5;

wherein R" is a monovalent group having from about 1 to about 20 carbon atoms, sulfur atoms, nitrogen atoms, oxygen atoms or a group containing combinations of the above atoms;

wherein the subscripts a, b, c, d, e, f and g are zero or positive and subject to the following limitations: 2≤a+b+c+d+e+f+g≤6000, and 0<b+d+f;

(c) a non-aqueous phase:

(d) an aqueous phase; and (e) optionally, one or more surfactants, active ingredients, and pigments.

BRIEF DESCRIPTION OF THE FIGURES

FIG. 1 shows rheology measurements of storage modules vs. shear stress for model high internal phase emulsions.

FIG. 2 shows rheology measurements of loss modules vs. shear stress for model high internal phase emulsions.

FIG. 3 is microscope images for model high internal phase emulsions.

FIG. 4 shows release of sodium salicylate from the skin cream formulations.

DETAILED DESCRIPTION OF PREFERRED EMBODIMENTS

The inventors herein have unexpectedly discovered a personal care composition which contains an acid functionality bearing silicone neutralized in situ with at least one aminosilane or a partially hydrolyzed aminosilane provides better stability to formulation in addition to improved delivery of hydrophilic actives from the formulation.

In the present invention, anionically modified silicones surprisingly showed an improved structuring of emulsions when used in presence of an amino functional silane or their hydrolyzates, giving an additional utility to improve the texture of such product without bringing an additional matrix building agents such as waxes. Furthermore, these systems provide enhanced delivery of actives that are typically present in dispersed aqueous phase of the formulations.

In the specification and claims herein, the following terms and expressions are to be understood as indicated herein below.

It will also be understood that any numerical range recited herein is intended to include all sub-ranges within that range and any combination of end points of said ranges or sub-ranges.

All methods described herein may be performed in any suitable order unless otherwise indicated or clearly contrary to context. The use herein of any and all examples or exemplification language (for example, such as), is intended merely to better illustrate the invention and does not pose a limitation on the scope of the invention unless otherwise claimed. No language in the specification should be construed as indicating any non-claimed element as essential to the practice of the invention.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

In one embodiment herein the personal care composition comprises
at least one polyorganosiloxane represented by the formula (I):

$$M^1_a M^2_b D^1_c D^2_d T^1_e T^2_f Q_g \qquad (I)$$

wherein:
$M^1 = R^1 R^2 R^3 SiO_{1/2}$
$M^2 = R^4 R^5 R^6 SiO_{1/2}$
$D^1 = R^7 R^8 SiO_{2/2}$
$D^2 = R^9 R^{10} SiO_{2/2}$
$T^1 = R^{11} SiO_{3/2}$
$T^2 = R^{12} SiO_{3/2}$
$Q = SiO_{4/2}$
wherein
$R^1$, $R^2$, $R^3$, $R^5$, $R^6$, $R^7$, $R^8$, $R^{10}$ and $R^{11}$ are aliphatic, aromatic or fluoro containing monovalent hydrocarbon groups containing from 1 to about 60 carbon atoms;

$R^4$, $R^9$ and $R^{12}$ are independently a monovalent group bearing an acid functional group selected from the group consisting of -A-COOH, -A-PO$_3$H, -A-OPO$_3$H, or -A-SO$_3$H, wherein A is selected from the group consisting of a divalent hydrocarbon group having from about 1 to about 60 carbon atoms, optionally substituted with heteroatoms, and a divalent arylalkylene group having the general formula —(CHR')$_k$C$_6$H$_4$(CH$_2$)$_h$—, —CH$_2$CH(R')(CH$_2$)$_k$C$_6$H$_4$—, and —CH$_2$CH(R')(CH$_2$)$_h$C$_6$H$_3$R"—;

wherein R' is hydrogen or an aliphatic, aromatic or fluoro containing monovalent hydrocarbon group having from 1 to about 60 carbon atoms, h has a value of 0 to 20, k has a value of 0 to 10, specifically from about 0 to about 5;

wherein R" is a monovalent group having from about 1 to about 20 carbon atoms, sulfur atoms, nitrogen atoms, oxygen atoms or a group containing combinations of the above atoms;

wherein the subscripts a, b, c, d, e, f and g are zero or positive and subject to the following limitations: 2≤a+b+c+d+e+f+g≤6000, and 0<b+d+f;

(c) a non-aqueous phase;
(d) an aqueous phase; and
(e) optionally, one or more surfactants, active ingredients, and pigments.

In one embodiment, the polyorganosiloxane is present in the composition in an amount ranging from 0.01% to 50% by weight, preferably from 0.1% to 25% and more preferably from 0.1% to 5% by weight relative to the total weight of the composition.

In a more specific embodiment, the monovalent hydrocarbon groups $R^1$, $R^2$, $R^3$, $R^5$, $R^6$, $R^7$, $R^8$, $R^{10}$, $R^{11}$ and R' are independently selected from the group consisting of methyl, ethyl, n-propyl, iso-propyl, n-butyl, isobutyl, tert-butyl, n-pentyl, iso-pentyl, neopentyl, tert-pentyl, hexyl, heptyl, octyl, isooctyl, 2,2,4-trimethylpentyl, nonyl, decyl, cycloalkyl groups and aryl groups.

In another specific embodiment, the aminosilane is represented by the formula (II):

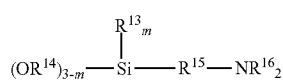

(II)

wherein $R^{13}$ is a monovalent substituted or unsubstituted hydrocarbon group of 1 to 13 carbon atoms; $R^{15}$ is a divalent alkyl or aryl group of 1 to 20 carbon atoms; $R^{16}$ is selected from hydrogen, ethyl, propyl and aminoethyl groups; $R^{14}$ is an aliphatic organic group selected from alkyl groups, alkylether groups, alkylester groups, alkylketone groups of 1 to 8 carbon atoms, an alkylcyano or an aralkyl group of 7 to 15 carbon atoms, subscript m has a value of 0 or 1.

In another more specific embodiment, the aminosilane is the reaction product of formula II with an oxirane containing compounds such the silanized amino copolymers prepared by the reaction of bis-epoxy compounds with amino silanes or combination of amino silane and other suitable amines.

In one embodiment, the aminosilane is present in the said personal care composition in an amount ranging from 0.01% to 25% by weight, preferably from 0.1% to 5% by weight relative to the total weight of the composition.

The condensation effective aminosilanes can be selected from alkoxy and acyloxy silanes bearing at least one amino group. Some examples of such silanes are γ-aminopropyl triethoxysilane, γ-aminopropyl trimethoxysilane, γ-aminopropylmethyl diethoxysilane, aminopropylmethyl dimethoxysilane, N-(β-aminoethyl)-γ-aminopropyl trimethoxysilane, triamino organosilanes, Bis-[γ-(triethoxysilyl)propyl]amine, Bis-[γ-(trimethoxysilyl)propyl]amine, N-phenyl-γ-aminopropyl trimethoxysilane, N-ethyl-γ-aminoisobutyl trimethoxysilane and combinations thereof.

In one embodiment the personal care formulation can be a personal care application selected from the group consisting of deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nail creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a more specific embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the crosslinked ionic silicone networks. Suitable personal care compositions may be in the form of an emulsion, including oil-in-water, water-in-oil and anhydrous emulsions, where in each of these emulsions the silicone phase may be either the discontinuous phase or the continuous phase, as well as multiple emulsions, such as, for example, oil-in-water-in-oil emulsions and water-in-oil-in-water emulsions; such as is described above.

In one useful embodiment, an antiperspirant composition comprises the acid functional silicone of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

In another useful embodiment, a skin care composition comprises the acid functional silicone and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylm ethane, p-aminobenzoic acid and octyl dimethyl-p-aminobenzoic acid.

In another useful embodiment, a color cosmetic composition, such as, for example, a lipstick, a makeup or a mascara composition comprises the crosslinked ionic silicone network, and a coloring agent, such as a pigment, a water soluble dye or a liposoluble dye.

Process of Preparing the Personal Care Composition

As stated above, there is provided herein a process of preparing a personal care composition comprising:

(a) at least one condensation effective aminosilane or hydrolysate thereof;

(b) at least one polyorganosiloxane represented by the formula (I) defined above (c) a non-aqueous phase;

(d) an aqueous phase; and (e) optionally, one or more surfactants, active ingredients, and pigments;

wherein the personal care composition is prepared by mixing the polyorganosiloxane (b), the non-aqueous phase (c), the aqueous phase (d), and optionally a surfactant (e), to form an primary emulsion, followed by the addition of the aminosilane (a).

In another embodiment, the personal care composition is prepared by mixing the aminosilane and the aqueous phase, and optionally a surfactant, followed by addition of the non-aqueous phase comprising the polyorganosiloxane.

In one embodiment, the polyorganosiloxane is present in the composition in an amount ranging from 0.01% to 50% by weight, preferably from 0.1% to 25% and more preferably from 0.1% to 5% by weight relative to the total weight of the composition.

In another embodiment, the aminosilane is present in the composition in an amount ranging from 0.01% to 25% by weight, preferably from 0.1% to 5% by weight relative to the total weight of the composition.

Various features of the invention are illustrated by the examples presented below.

EXAMPLES

Example 1: Preparation of Carboxy End-Capped PDMS

Carboxy end capped silicone with average molecular formula $HOOC(CH_2)_{10}Si(CH_3)_2O((CH_3)_2SiO)_{100}Si(CH_3)_2(CH_2)_{10}COOH$ was prepared by hydrosilylation of corresponding hydride functional silicone with trimethyl silyl ester of undecenoic acid at 80° C. using 10 ppm of Pt(0) catalyst until hydrides are consumed fully as confirmed by 1H-NMR. This was followed by deprotection of the silyl ester at 60° C. using 2 times molar excess of ethanol for 4-6 hr. Upon stripping the material at 130° C. at 50 mbar pressure yields the said carboxy end-capped silicone with 0.34 meq/g of acid content and viscosity of 256 cp.

Water in Oil High Internal Phase Emulsion Formulations 1-5 (F1-F5) Using the Carboxylate Silicone of Example 1

High internal phase (HIP) emulsions were prepared according to Table 1 by separately mixing the oil phase comprising the carboxylate silicone of Example 1 and a primary surfactant Silsoft 1540 and the aqueous phase, followed by slow addition of the aqueous phase to oil. Once addition is complete the emulsion is mixed for another 30 mins and the other additives are added and mixed for another 30 mins to produce the emulsion. The resulting high internal phase emulsion is then characterized with rheology experiments, microscopy and stability studies at 50° C.

TABLE 1

Formulations 1-5

|  |  | Formulations | | | | |
| --- | --- | --- | --- | --- | --- | --- |
|  |  | F1 | F2 | F3 | F4 | F5 |
| Oil Phase | Cyclopentasiloxane | 20 | 20 | 20 | 20 | 20 |
|  | Silsoft 1540 from Momentive Performance Materials Inc. | 3 | 3 | 3 | 3 | 3 |
|  | Carboxylate silicone of Example 1 | 3 | 3 | 3 | 3 | 3 |
| Aqueous Phase | Water | 69 | 69 | 69 | 69 | 69 |
|  | Glycerin from Sigma Aldrich | 4 | 4 | 4 | 4 | 4 |
|  | NaCl from Sigma Aldrich | 1 | 1 | 1 | 1 | 1 |
| Other additives | Silquest A-1100 from Momentive Performance Materials Inc. |  | 0.5 | 0.180 |  |  |
|  | Triethylamine from Sigma Aldrich |  |  |  | 0.100 |  |
|  | A-1630 from Momentive Performance Materials Inc. |  |  |  |  | 0.135 |

Rheology Measurements

Rheology measurements were performed in Haake Rheometer at 25° C. and indicated better structuring with the composition according to the present invention over the control samples.

The results are showing in FIGS. 1 and 2. In the figures the formulations according to present invention provide better modulus or structuring over competitive examples.

Microscope Images

In microscopic images the internal phase droplet size was significantly reduced upon neutralization of the silicone carboxy acid of example 1 (formulation F2, F3 and F4) indicating enhance interfacial activity of the carboxy silicone. The results are showing in FIG. 3.

Cream Formulations Comprising Actives and Release Studies

Skin cream formulations containing actives were prepared according to Table 2 in the same manner as described previously. For the study, Sodium Salicylate was used as model for water soluble active. In the Comparative Sample, a silicone cross-polymer was used as structuring agent.

TABLE 2

|  | Formulations | Test Sampl | Comparative Sample |
|---|---|---|---|
| Base Oil | Crodamol IPM from Croda | 5 | 5 |
|  | Paraffin Oil from Sigma Aldrich | 5 | 5 |
|  | SF 1202 from Momentive Performance Materials Inc. | 7 | 7 |
|  | SF-1540 from Momentive Performance Materials Inc. | 2 | 2 |
|  | Silicone Cross-polymer |  | 3 |
|  | Carboxylate silicone of Example 1 | 3 |  |
| Aqueous Phase | Water | 69.5 | 70 |
|  | Glycerin from Sigma Aldrich | 4 | 4 |
|  | NaCl from Sigma Aldrich | 1 | 1 |
|  | Sodium Salicylate from Sigma Aldrich | 3 | 3 |
|  | A-1100 Silane from Momentive Performance Materials Inc. | 0.5 |  |

The release studies were performed on a Franz Diffusion Cell. The formulation were applied on to a Millipore Membrane with 400 nm pore size and then placed in between the donor and acceptor compartments and the active released across the membrane in to the acceptor compartment holding water was measured using HPLC technique.

The results are showing in FIG. 4. As can be seen from FIG. 4, the test formulation comprising silane-silicone carboxylate structuring agent comprising formulation showed faster delivery of active across a model membrane.

These examples are to be construed as exemplary in nature only and are not intended in any way to limit the appended claims. It is contemplated that a person having ordinary skill in the art would be able to produce obvious variations of the subject matter and disclosures herein contained that would be by reason of such ordinary skill within the literal or equitable scope of the appended claims.

The invention claimed is:

1. A personal care composition comprising:
   (a) at least one condensation effective aminosilane or hydrolysate thereof;
   (b) at least one polyorganosiloxane represented by the formula (I):

$$M^1_a M^2_b D^1_c D^2_d T^1_e T^2_f Q_g \qquad (I)$$

wherein:
$M^1 = R^1 R^2 R^3 SiO_{1/2}$
$M^2 = R^4 R^5 R^6 SiO_{1/2}$
$D^1 = R^7 R^8 SiO_{2/2}$
$D^2 = R^9 R^{10} SiO_{2/2}$
$T^1 = R^{11} SiO_{3/2}$
$T^2 = R^{12} SiO_{3/2}$
$Q = SiO_{4/2}$ wherein
$R^1$, $R^2$, $R^3$, $R^5$, $R^6$, $R^7$, $R^8$, $R^{10}$ and $R^{11}$ are independently aliphatic, aromatic or fluoro containing monovalent hydrocarbon groups containing from 1 to about 60 carbon atoms;

$R^4$, $R^9$ and $R^{12}$ are independently a monovalent group bearing an acid functional group selected from the group consisting of -A-COOH, -A-PO$_3$H, -A-OPO$_3$H and -A-SO$_3$H, wherein A is selected from the group consisting of a divalent hydrocarbon group having from about 1 to about 60 carbon atoms and a divalent arylalkylene group having the general formula —(CHR')$_k$C$_6$H$_4$(CH$_2$)$_h$—, —CH$_2$CH(R')(CH$_2$)$_k$C$_6$H$_4$—, and —CH$_2$CH(R')(CH$_2$)$_h$C$_6$H$_3$R"—, wherein when A is the divalent hydrocarbon group, it is optionally substituted with heteroatoms;

wherein R' is selected from the group consisting of hydrogen, an aliphatic having from 1 to about 60 carbon atoms, an aromatic containing monovalent hydrocarbon group having from 1 to about 60 carbon atoms and a fluoro containing monovalent hydrocarbon group having from 1 to about 60 carbon atoms, h has a value of 0 to 20, k has a value of 0 to 10;

wherein R" is a monovalent group having from about 1 to about 20 carbon atoms, sulfur atoms, nitrogen atoms, oxygen atoms or a group containing combinations of the above atoms;

wherein the subscripts a, b, c, d, e, f and g are zero or positive and subject to the following limitations: 2≤a+b+c+d+e+f+g≤6000, and 0<b+d+f;

(c) a non-aqueous phase;
   (d) an aqueous phase; and
   (e) optionally, one or more surfactants, active ingredients, and pigments.

2. The personal care composition of claim 1 wherein the monovalent hydrocarbon groups $R^1$, $R^2$, $R^3$, $R^5$, $R^6$, $R^7$, $R^8$, $R^{10}$, $R^{11}$ and R' are independently selected from the group consisting of methyl, ethyl, n-propyl, iso-propyl, n-butyl, isobutyl, tert-butyl, n-pentyl, iso-pentyl, neopentyl, tert-pentyl, hexyl, heptyl, octyl, isooctyl, 2,2,4-trimethylpentyl, nonyl, decyl, cycloalkyl groups and aryl groups.

3. The personal care composition of claim 2 wherein the cycloalkyl groups are independently selected from the group consisting of cyclopentyl, cyclohexyl, cycloheptyl and methylcyclohexyl groups.

4. The personal care composition of claim 2 wherein the aryl groups are independently selected from the group consisting of phenyl, naphthyl, o-tolyl, m-tolyl, p-tolyl, xylyl, ethylphenyl and benzyl.

5. The personal care composition of claim 1 wherein at least one of $R^4$, $R^9$ and $R^{12}$ is a monovalent group bearing an acid functional group selected from the group consisting of -A-COOH, -A-PO$_3$H, -A-OPO$_3$H and -A-SO$_3$H.

6. The personal care composition of claim 1 wherein the at least one condensation effective aminosilane is represented by the formula (II):

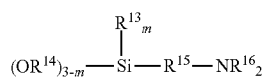
(II)

wherein $R^{13}$ is a monovalent substituted hydrocarbon group of 1 to 13 carbon atoms or unsubstituted hydrocarbon group of 1 to 13 carbon atoms; $R^{15}$ is a divalent alkyl group of 1 to 20 carbon atoms or aryl group of 1 to 20 carbon atoms; $R^{16}$ is selected from hydrogen, ethyl, propyl and aminoethyl groups; $R^{14}$ is an aliphatic organic group selected from alkyl groups of 1 to 8 carbon atoms, alkylether groups of 1 to 8 carbon atoms, alkylester groups of 1 to 8 carbon atoms, alkylketone groups of 1 to 8 carbon atoms, an alkylcyano group of 7 to 15 carbon atoms or an aralkyl group of 7 to 15 carbon atoms, subscript m has a value of 0 or 1.

7. The personal care composition of claim 1 wherein the at least one condensation effective aminosilane is an alkoxysilane comprising one or more primary and/or secondary amine functional groups.

8. The personal care composition of claim 1 wherein the at least one condensation effective aminosilane is chosen from γ-aminopropyl triethoxysilane, γ-aminopropyl trimethoxysilane, γ-aminop(Currently Amended) ropylmethyl diethoxysilane, aminopropylmethyl dimethoxysilane, N-(β-aminoethyl)-γ-aminopropyl trimethoxysilane, triamino organosilanes, Bis[γ-(triethoxysilyl)propyl]amine, Bis-[γ-(trimethoxysilyl)propyl]amine, N-phenyl-γ-aminopropyl trimethoxysilane, N-ethyl-γ-aminoisobutyl trimethoxysilane and combinations thereof.

9. The personal care composition of claim 1 wherein the at least one condensation effective aminosilane is selected from the group consisting of 3-aminopropyltriethoxysilane, 3-aminopropylmethyldiethoxysilane, N-(2-aminoethyl)-3-aminopropyltriethoxysilane, 3-(2-aminoethylamino)propylmethyldiethoxysilane and combinations thereof.

10. The personal care composition of claim 1 wherein the at least one condensation effective aminosilane is present in the composition in an amount ranging from 0.01% to 25% by weight of the personal care composition.

11. The personal care composition of claim 1 wherein the at least one polyorganosiloxane is present in the composition in an amount ranging from 0.01% to 50% by weight of the personal care composition.

12. The personal care composition of claim 1 wherein the personal care composition further comprises solvents selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

13. The personal care composition of claim 1 wherein the aqueous phase comprises water or an aqueous solution containing personal care ingredients.

14. The personal care composition of claim 1 wherein the personal care composition is an oil-in-water, a water-in-oil or a multiple emulsion.

15. The personal care composition of claim 1 wherein the surfactants are ionic, nonionic, polymeric or mixtures thereof.

16. The personal care composition of claim 1 wherein the active ingredients include bioactives, anti-acne agents, anti-ageing agents, anti-caries agents, anti-fungal agents, anti-microbial agents, anti-oxidants, anti-cancer, anti-viral, anti-inflammatory, anti-coagulants, hemostatic agents, exfoliants, hormones, hormone analogs, enzymes, proteins and peptides, medicinal compounds, biocides, external analgesics, oral care agents, oral care drugs, oxidizing agents, reducing agents, skin protectants, essential oils, insect repellents, UV light absorbing agents, solar filters, pigments, hydrating agents, vitamins and combinations thereof.

17. A personal care application comprising the personal care composition of claim 1 wherein the personal care application is selected from the group consisting of a skin care application, a cosmetic application, a hair care application and a keratin-shaping application.

18. A process of preparing a personal care composition comprising:
(a) at least one condensation effective aminosilane or hydrolysate thereof;
(b) at least one polyorganosiloxane represented by the formula (I):

(I)

wherein:
$M^1 = R^1R^2R^3SiO_{1/2}$
$M^2 = R^4R^5R^6SiO_{1/2}$
$D^1 = R^7R^8SiO_{2/2}$
$D^2 = R^9R^{10}SiO_{2/2}$
$T^1 = R^{11}SiO_{3/2}$
$T^2 = R^{12}SiO_{3/2}$
$Q = SiO_{4/2}$ wherein
$R^1$, $R^2$, $R^3$, $R^5$, $R^6$, $R^7$, $R^8$, $R^{10}$ and $R^{11}$ are independently aliphatic, aromatic or fluoro containing monovalent hydrocarbon groups containing from 1 to about 60 carbon atoms;
$R^4$, $R^9$ and $R^{12}$ are independently a monovalent group bearing an acid functional group selected from the group consisting of -A-COOH, -A-PO$_3$H, -A-OPO$_3$H, or -A-SO$_3$H,
wherein A is selected from the group consisting of a divalent hydrocarbon group having from about 1 to about 60 carbon atoms and a divalent arylalkylene group having the general formula —(CHR')$_k$C$_6$H$_4$(CH$_2$)$_h$—, —CH$_2$CH(R')(CH$_2$)$_k$C$_6$H$_4$—, and —CH$_2$CH(R')(CH$_2$)$_h$C$_6$H$_3$R''—, wherein when A is the divalent hydrocarbon group, it is optionally substituted with heteroatoms;
wherein R' is selected from the group consisting of hydrogen, an aliphatic having from 1 to about 60 carbon atoms, an aromatic containing monovalent hydrocarbon group having from 1 to about 60 carbon atoms and a fluoro containing monovalent hydrocarbon group having from 1 to about 60 carbon atoms, h has a value of 0 to 20, k has a value of 0 to 10;
wherein R" is a monovalent group having from about 1 to about 20 carbon atoms, sulfur atoms, nitrogen atoms, oxygen atoms or a group containing combinations of the above atoms;

wherein the subscripts a, b, c, d, e, f and g are zero or positive and subject to the following limitations: $2 \leq a+b+c+d+e+f+g \leq 6000$, and $0<b+d+f$;

(c) a non-aqueous phase;

(d) an aqueous phase; and (e) optionally, one or more surfactants, active ingredients, and pigments;

wherein the personal care composition is prepared by mixing the at least one polyorganosiloxane (b), the non-aqueous phase (c), the aqueous phase (d), and optionally a surfactant (e), to form an primary emulsion, followed by the addition of the at least one condensation effective aminosilane (a).

19. A process of preparing a personal care composition comprising (a) at least one condensation effective aminosilane or hydrolysate thereof;

(b) at least one polyorganosiloxane represented by the formula (I):

$$M^1_a M^2_b D^1_c D^2_d T^1_e T^2_f Q_g \quad (I)$$

wherein:

$M^1 = R^1 R^2 R^3 SiO_{1/2}$
$M^2 = R^4 R^5 R^6 SiO_{1/2}$
$D^1 = R^7 R^8 SiO_{2/2}$
$D^2 = R^9 R^{10} SiO_{2/2}$
$T^1 = R^{11} SiO_{3/2}$
$T^2 = R^{12} SiO_{3/2}$
$Q = SiO_{4/2}$ wherein $R^1, R^2, R^3, R^5, R^6, R^7, R^8, R^{10}$ and $R^{11}$ are independently aliphatic, aromatic or fluoro containing monovalent hydrocarbon groups containing from 1 to about 60 carbon atoms;

$R^4, R^9$ and $R^{12}$ are independently a monovalent group bearing an acid functional group selected from the group consisting of -A-COOH, -A-$PO_3H$, -A-$OPO_3H$, or -A-$SO_3H$, wherein A is selected from the group consisting of a divalent hydrocarbon group having from about 1 to about 60 carbon atoms and a divalent arylalkylene group having the general formula —(CHR')$_k C_6 H_4$ (CH$_2$)$_h$—, —CH$_2$CH(R')(CH$_2$)$_k C_6 H_4$—, and —CH$_2$CH(R')(CH$_2$)$_h C_6 H_3 R''$—, wherein when A is the divalent hydrocarbon group, it is optionally substituted with heteroatoms;

wherein R' is selected from the group consisting of hydrogen, an aliphatic having from 1 to about 60 carbon atoms, an aromatic containing monovalent hydrocarbon group having from 1 to about 60 carbon atoms and a fluoro containing monovalent hydrocarbon group having from 1 to about 60 carbon atoms, h has a value of 0 to 20, k has a value of 0 to 10;

wherein R'' is a monovalent group having from about 1 to about 20 carbon atoms, sulfur atoms, nitrogen atoms, oxygen atoms or a group containing combinations of the above atoms;

wherein the subscripts a, b, c, d, e, f and g are zero or positive and subject to the following limitations: $2 \leq a+b+c+d+e+f+g \leq 6000$, and $0<b+d+f$;

(c) a non-aqueous phase;

(d) an aqueous phase; and (e) optionally, one or more surfactants, active ingredients, and pigments, wherein the personal care composition is prepared by mixing the at least one condensation effective aminosilane (a), the aqueous phase (d), and optionally a surfactant (e), followed by the addition of the at least one polyorganosiloxane (b) and the non-aqueous phase (c).

* * * * *